United States Patent [19]

Misaki et al.

[11] 4,122,251
[45] Oct. 24, 1978

[54] PROCESS FOR PRODUCTION OF 5-FLUOROURACIL AND ITS DERIVATIVES

[75] Inventors: Susumu Misaki, Mino; Sadamu Ishii, Osaka; Nobuyuki Suzuki, Nobeoka; Mikio Wakabayashi, Nobeoka; Tsuneo Sowa, Nobeoka, all of Japan

[73] Assignees: Daikin Kogyo Co., Ltd.; Asahi Chemical Industry Co., Ltd., both of Japan

[21] Appl. No.: 805,031

[22] Filed: Jun. 9, 1977

[30] Foreign Application Priority Data

Jun. 11, 1976 [JP] Japan .................................. 51-69003

[51] Int. Cl.$^2$ ..................... C07D 239/54; C07H 19/06
[52] U.S. Cl. ......................................... 536/23; 544/313
[58] Field of Search ........................... 260/260; 536/23

[56] References Cited

U.S. PATENT DOCUMENTS

| | | | |
|---|---|---|---|
| 2,802,005 | 8/1957 | Heidelberger | 260/260 |
| 3,635,977 | 1/1972 | Lutz | 260/260 |
| 3,682,917 | 8/1972 | Knuniants et al. | 260/260 |
| 3,954,758 | 5/1976 | Schuman et al. | 260/260 |
| 4,029,661 | 6/1977 | Schuman et al. | 260/260 |

Primary Examiner—Paul M. Coughlan, Jr.
Attorney, Agent, or Firm—Birch, Stewart, Kolasch and Birch

[57] ABSTRACT

A process for production of 5-fluorouracil and its derivatives which comprises reacting a cytosine compound of the formula:

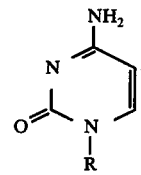

wherein R is a hydrogen atom or a saccharide residue with fluorine or fluorine fluorosulfonate (FOSO$_2$F) in an aqueous medium to give the corresponding 5-fluorouracil compound of the formula:

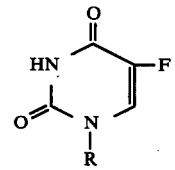

wherein R is as defined above.

19 Claims, No Drawings

PROCESS FOR PRODUCTION OF 5-FLUOROURACIL AND ITS DERIVATIVES

The present invention relates to a process for production of 5-fluorouracil and its derivatives. More particularly, it relates to a process for preparing 5-fluorouracil and its derivatives (hereinafter referred to as "5-fluorouracil compound(s)") from the corresponding cytosine and its $N^1$-derivatives.

For production of 5-fluorouracil compounds, which are known to be useful as anti-tumor agents of the metabolic antagonist type or intermediates in the synthesis of such agents, there is proposed a process which comprises the step of direct fluorination of uracil with fluorine [cf. U.S. Pat. No. 3,682,917].

As the result of an extensive study seeking an advantageous process for production of 5-fluorouracil compounds, it has been found that the fluorination of cytosine compounds by the use of fluorine or fluorine fluorosulfonate can afford the corresponding 5-fluorouracil compounds in excellent yields. While it is known that the fluorination of cytosine with trifluoromethyl hypofluorite affords 5-fluorocytosine [M. J. Robins et al.: J. Chem. Soc., Chem. Comm., 18, (1972)], the direct production of any fluorinated uracil compound from the corresponding cytosine compound by fluorination has never been known.

According to the present invention, the cytosine compound of the formula (I):

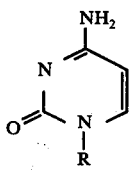

wherein R is a hydrogen atom or a saccharide residue is reacted with fluorine or fluorine fluorosulfonate in an aqueous medium to give the corresponding 5-fluorouracil compound of the formula (II):

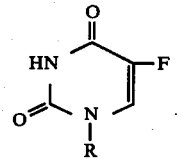

wherein R is as defined above.

As the starting cytosine compound (I), there may be used cytosine or its derivative having a saccharide residue at the $N^1$-position in a free or salt form. Examples of the saccharide residue include the residues of pentoses (e.g. ribose, deoxyribose, arabinose, lyxose, xylose) and of hexoses (e.g. glucose, fructose). The saccharide residue usually has at least one hydroxyl group, and such hydroxyl group may be preferably converted into protected hydroxyl prior to the use in the reaction. The conversion of the hydroxyl group into protected hydroxyl can be achieved by conventional procedures, and examples of the protective group are acetyl, benzoyl, isopropylidene, etc.

The reaction is carried out in an aqueous medium which may consist of water alone or a mixture of water with at least one other solvent such as inorganic acids (e.g. sulfuric acid, hydrogen fluoride), organic acids (e.g. acetic acid, trifluoroacetic acid, polyfluoropropionic acid), alcohols (e.g. ethanol, trifluoroethanol), halogenated ketones (e.g. hexafluoroacetone hydrate) and halogenated hydrocarbons (e.g. chloroform, carbon tetrachloride, trichlorotrifluoroethane). The use of water alone is particularly preferred. However, the presence of water in the reaction system is not necessarily required from the beginning of the reaction. For instance, water may be added to the reaction system containing or not containing any other solvent in the course of the reaction so as to make it aqueous.

In one of the typical procedures for carrying out the process of this invention, the cytosine compound (I) is dissolved or suspended in the aqueous medium, followed by introduction of fluorine or fluorine fluorosulfonate as the fluorinating agent into the resulting solution or suspension. Fluorine fluorosulfonate is a gaseous material at room temperature under atmospheric pressure and can be easily produced by the reaction between fluorine and sulfuric acid anhydride. Fluorine or fluorine fluorosulfonate may be used as such or in a dilute form with an inert gas such as nitrogen, argon or carbon dioxide. The amount of these fluorinating agents to be used for completion of the reaction is normally from about 1 to 6 mol to 1 mol of the cytosine compound (I). In case of using fluorine, the presence of a hydrogen sulfite ion liberated, for instance, from sodium hydrogensulfite or potassium hydrogensulfite in an equimolar amount or less with respect to the cytosine compound (I) is preferred, since the reaction proceeds to give a better result.

The reaction is usually carried out at room temperature. When, however, the saccharide residue present in the cytosine compound (I) or the hydroxyl group or its protective group existing in such saccharide residue is not sufficiently stable under an acidic condition, for instance, as seen in case of 2'-deoxyribose, it will be necessary to effect the reaction at a temperature below room temperature. For completion of the reaction within a shorter period of time, a higher temperature is necessitated. If desired, the temperature may be elevated gradually from the beginning of the reaction to the end.

The process of the reaction can be traced by checking the consumption of the cytosine compound (I) or the variation in the ultraviolet absorption spectrum of the reaction mixture. When the reaction is effected under a relatively mild condition, for instance, at a temperature lower than room temperature, it is frequently observed that the amount of the produced 5-fluorouracil compound (II) is small in relation to the amount of the consumed cytosine compound (I). This is due to the production of an intermediary compound. In such case, the yield of the objective 5-fluorouracil compound (II) can be enhanced by heating the reaction mixture so as to convert the intermediary compound into the 5-fluorouracil compound (II). Preferably, the heating is applied to the reaction mixture, which is usually as such strongly acidic and has a pH of less than about 1, after adjustment of the pH to about 1 to 9 with an aqueous alkaline solution. The temperature on heating is somewhat higher than that as adopted in the reaction with the said fluorinating agent and may be usually from about 60° to 100° C. The conversion is ordinarily accomplished within a period of 1 to 6 hours. However, heating under a strongly alkaline condition or for a too long period of time is not preferred, since some by-products are produced. When heating is effected at a temperature below about 60° C., there is seen a tendency that the conversion into the 5-fluorouracil compound (II) becomes slow.

For recovery of the produced 5-fluorouracil compound (II), the reaction mixture is, for instance, concentrated by distillation and the residue is purified by a conventional procedure such as recrystallization from water or an organic solvent (e.g. ethanol) or chromatography on ion exchange resins.

The process of this invention is advantageous in simultaneous achievement of fluorination and deamination of the cytosine compound (I) so as to afford the corresponding 5-fluorouracil (II) in high yields with ease.

Practical and presently preferred embodiments of the present invention are illustratively shown in the following examples wherein the thin layer chromatography was carried out using a mixture of ethyl acetate:acetone:water (7:4:1 by weight) as the solvet for development and silica gel 60 $F_{254}$ (manufactured by E. Merck A.G.) as the carrier, and the paper chromatography was effected by the use of a supernatant of a mixture of n-butanol:acetic acid:water (4:1:5 by weight) as the solvent for development and Toyo Roshi No. 51 as the filter paper.

EXAMPLE 1

Into a "Daiflon" resin (polytriflurochloroethylene manufactured by Daikin Kogyo, Co., Ltd.) made flask equipped with a stirrer, a cooler, a gas inlet and a therometer, a solution of cytosine (1.11 g; 10 mmol) in water (50 ml) was charged, and fluorine gas (34%; diluted with nitrogen) was blown therein at 18° to 20° C. until the cytosine was consumed completely. The reaction was finished in 60 minutes, and the total amount of fluorine used was 35 mmol. The reaction mixture (pH, <1) was adjusted to pH 6.0 with an aqueous solution of sodium hydroxide and heated at 80° C. for 4 hours. After removal of the solvent while heating under reduced pressure, the residual pale brown solid was extracted with ethanol and recrystallized from water to give 5-fluorouracil (0.85 g). Yield, 65%. M.P. 282°–283° C. (decomp.). UV absorption spectrum: $\lambda_{max}^{pH 2}$ 266 nm; $\lambda_{max}^{pH 10.5}$ 269 nm. Thin layer chromatography: Rf 0.60. Paper chromatography: Rf 0.54.

EXAMPLE 2

The reaction and the treatment were carried out in the same manner as in Example 1 but adjusting the reaction mixture after the fluorination to pH 6 and then heating at 60° C. for 5 hours to give 5-fluorouracil (0.25 g). Yield, 19%.

EXAMPLE 3

The reaction and the treatment were carried out in the same manner as in Example 1 but heating the reaction mixture after the fluorination at 80° C. for 4 hours without previous pH adjustment to give 5-fluorouracil (0.72 g). Yield, 55%.

EXAMPLE 4

The reaction and the treatment were carried out in the same manner as in Example 1 but adjusting the reaction mixture after the fluorination to pH 10 and then heating at 80° C. for 4 hours to give 5-fluorouracil (0.46 g). Yield, 35%.

EXAMPLE 5

The reaction and the treatment were carried out in the same manner as in Example 1 but adjusting the reaction mixture after the fluorination to pH 6.0 and then heating at 80° C. for 14 hours to give 5-fluorouracil (0.18 g). Yield, 14%.

EXAMPLE 6

Into a solution of cytosine (1.11 g; 10 mmol) in water (50 ml), fluorine gas was blown at 40° to 50° C. until the cytosine was completely consumed. The reaction was finished in 35 minutes, and the total amount of fluorine used was 20 mmol. The reaction mixture was heated at 80° C. for 4 hours, and the solvent was removed by distillation under reduced pressure. The residual pale brown solid was extracted with ethanol and recrystallized from water to give 5-fluorouracil (0.87 g). Yield, 67%.

EXAMPLE 7

The reaction and the treatment were carried out in the same manner as in Example 1 but using a solution of cytosine (1.11 g; 10 mmol) and sodium hydrogensulfite (1.56 g; 15 mmol) in water (50 ml) to give 5-fluorouracil (0.98 g). Yield, 75.4%.

EXAMPLE 8

The reaction and the treatment were carried out in the same manner as in Example 1 but using a solution of cytosine hydrochloride (1.47 g) in water (50 ml) to give 5-fluorouracil (9.86 g). Yield, 66%.

EXAMPLE 9

The reaction and the treatment were carried out in the same manner as in Example 1 but using a solution of cytosine (1.11 g; 10 mmol) in a mixture of acetic acid (30 ml) and water (20 ml) to give 5-fluorouracil (0.78 g). Yield, 60%.

EXAMPLE 10

The reaction and the treatment were carried out in the same manner as in Example 1 but using a solution of cytosine (1.11 g) in 2,2,2-trifluoroetanol (100 ml) and blowing the fluorine gas therein at 20° C. to give 5-fluorouracil (0.72 g). Yield, 55%.

EXAMPLE 11

Into a solution of cytosine (1.11 g; 10 mmol) in water (100 ml), fluorine fluorosulfonate (60%; diluted with nitrogen) was blown until the cytosine was completely consumed. The reaction was finished in 75 minutes, and the total amount of fluorine fluorosulfonate used was 15 mmol. The reaction mixture (pH, 1.0) was adjusted to pH 8.0 with sodium hydroxide and heated at 80° C. for 3 hours, during which the pH changed to 6.2. The reaction mixture was concentrated under reduced pressure, and the residual pale yellow solid was washed with ethanol and recrystallized from water to give 5-fluorouracil (1.14 g). Yield, 87.7%.

EXAMPLE 12

The reaction and the treatment were carried out in the same manner as in Example 11 but heating the reaction mixture after the fluorination at 80° C. for 4 hours without previous pH adjustment to give 5-fluorouracil (0.94 g). Yield, 72.3%.

EXAMPLE 13

Into a solution of cytosine (11.1 g) in a mixture of trifluoracetic acid (80 ml) and water (10 ml) kept at 10° C., fluorine fluorosulfonate was blown while stirring. The cytosine was completely consumed in 90 minutes, and the total amount of fluorine fluorosulfonate used was 18 mmol. The reaction mixture was heated under reflux for 4 hours and then treated as in Example 11 to give 5-fluorouracil (10.4 g). Yield, 80%.

EXAMPLE 14

Into a solution of cytosine (11.1 g) in hydrogen fluoride (50 ml) kept at 5° C., fluorine fluorosulfonate was blown while stirring. The cytosine was completely consumed in 2 hours, and the total amount of fluorine fluorosulfonate was 0.21 mol. The reaction mixture was heated to distill out the hydrogen fluoride, water (100 ml) was added thereto, and the resulting mixture was heated under reflux for 2 hours. An aqueous solution of calcium hydroxide was added thereto to make pH 6, and precipitated materials were eliminated by filtration. The filtrate was cooled, and the separated crystals were collected by filtration to give 5-fluorouracil (9.9 g). Yield, 76.2%.

EXAMPLE 15

Into a solution of cytosine (11.1 g) in 1 N sulfuric acid (100 ml) kept at 20° C., fluorine fluorosulfonate (60%; diluted with nitrogen) was blown while stirring. The cytosine was completely consumed in 1.5 hours, and the total amount of fluorine fluorosulfonate was 0.2 mol. The reaction mixture was heated at 90° C. for 3 hours. An aqueous solution of calcium hydroxide was added thereto to make pH 6, and precipitated materials were eliminated by filtration. The filtrate was cooled, and the separated crystals were collected by filtration to give 5-fluorouracil (8.1 g). Yield, 62.3%.

EXAMPLE 16

Into a solution of arabinocytosine (2.43 g; 10 mmol) in water (30 ml) kept at 5° C., fluorine gas (34%; diluted with nitrogen) was blown. The reaction was completed in 60 minutes, and the total amount of fluorine used was 35 mmol. The reaction mixture (pH 1.0) was adjusted to pH 8.0 with sodium hydroxide, heated at 80° C. for 4 hours and then passed through a column of activated charcoal in pellets, followed by elution with 1 N ammonia water. The fractions containing the objective 5-fluorinated product were collected and concentrated, and the residue was crystallized from ethanol to give 5-fluoroarabinouracil (1.35 g). Yield, 51.5%. M.P. 195.5° to 197° C. UV absorption spectrum: $\lambda_{max}^{pH2}$ 269.5 nm; $\lambda_{max}^{pH\,10.5}$ 268 nm. Thin layer chromatography: Rf 0.55. Paper chromatography: Rf 0.50.

EXAMPLE 17

Into a solution of arabinocytosine (2.43 g; 10 mmol) in water (30 ml) kept at 5° C., fluorine fluorosulfonate (50%, diluted with nitrogen) was blown, during which the temperature was elevated gradually to room temperature in 2 hours. The total amount of fluorine fluorosulfate used was 20 mmol. The reaction mixture (pH 1.0) was adjusted to pH 8.0 with an aqueous solution of sodium hydroxide, heated at 80° C. for 3 hours and then passed through a column of activated charcoal in pellets, followed by elution with 1 N ammonia water. The fractions containing the objective 5-fluorinated product were collected and concentrated, and the residue was crystallized from ethanol to give 5-fluoroarabinouracil (1.65 g). Yield, 62.9%. M.P. 195.5° to 197° C.

EXAMPLE 18

The reaction and the treatment were carried out in the same manner as in Example 16 but using cytidine (10 mmol) in place of cytosine to give 5-fluorouridine (1.22 g). Yield, 46.6%. M.P. 183° to 185° C. UV absorption spectrum: $\lambda_{max}^{pH2}$ 268 nm; $\lambda_{max}^{pH\,10.0}$ 268 nm. Thin layer chromatography: Rf 0.40. Paper chromatography: Rf 0.37.

EXAMPLE 19

Into a solution of 2',3',5'-triacetylcytidine (3.69 g; 10 mmol) in chloroform (50 ml) kept at 10° C., fluorine fluorosulfonate (60%; diluted with nitrogen) was blown, during which the temperature was gradually elevated to room temperature in 1.5 hours. After removal of the solvent by distillation under reduced pressure, the residue was dissolved in a mixture of water and ethanol (1:2 by volume), and the resulting solution was adjusted to pH 8 with an aqueous solution of calcium hydroxide. The precipitate was eliminated by filtration, and the filtrate was heated at 80° C. for 3 hours. After cooling, conc. ammonia water was added thereto to make pH 11. The resultant mixture was allowed to stand overnight and concentrated to dryness. The residue was crystallized from ethanol to give 5-fluorouridine (1.99 g). Yield, 76%.

EXAMPLE 20

As in Example 19, 3',5'-diacetyl-2'-deoxycytidine (3.11 g; 10 mmol) was fluorinated. The reaction mixture was neutralized with 1 N ammonia water to make pH 7.5 and heated at 70° C. for 3 hours. After cooling, the water layer was extracted with chloroform, and the chloroform extract was combined with the organic layer, washed with water, dried over anhydrous magnesium sulfate and concentrated under reduced pressure. The residue was dissolved in ether, filtered and concentrated to dryness. This operation was repeated three times, and then the resultant product was dried in vacuo to give 3',5'-diacetyl-2'-deoxy-5-fluorouracil (1.19 g). Yield, 36%. M.P. 150° to 153° C. UV absorption spectrum: $\lambda_{max}^{pH2}$ 268 nm. Thin layer chromatography: Rf 1.0, Rf 0.58 (ethyl acetate).

EXAMPLE 21

Into a solution of 2', 3',5'-tribenzoylcytidine hydrochloride (1.77 g; 3 mmol) in a mixture of chloroform:ethanol (3:1 by volume; 100 ml) kept at 18° C., fluorine fluorosulfonate (50%; diluted with nitrogen) was blown. The reaction was completed in 2 hours, and the total amount of fluorine used was 10 mmol. The reaction mixture was adjusted to pH 7 with ammonia water and heated at 70° C. for 4 hours. The solvent was distilled under reduced pressure. The residue was extracted with hot toluene, the toluene extract was filtered and the filtrate was concentrated and cooled to give 2',3',5'-tribenzoyl-5-fluorouridine (1.07 g). Yield, 75.2%. M.P. 210° to 214° C.

What is claimed is:

1. A process for the production of 5-fluorouracil and derivatives thereof which comprises the step of reacting a cytosine compound of the formula:

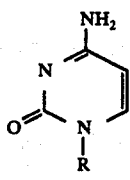

wherein R is a hydrogen atom or a saccharide residue with fluorine in the presence of a hydrogen sulfite or with fluorine fluorosulfonate in an aqueous medium to give the corresponding 5-fluorouracil compound of the formula:

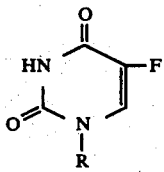

wherein R is as defined above.

2. The process according to claim 1, wherein R is a hydrogen atom.

3. The process according to claim 1, wherein R is a saccharide residue.

4. The process according to claim 3, wherein the saccharide residue is the residue of pentose or hexose.

5. The process according to claim 4, wherein the hydroxyl groups in the residue of pentose or hexose are protected.

6. The process according to claim 5, wherein the protective group for the hydroxyl groups is acetyl or benzoyl.

7. The process according to claim 1, wherein the aqueous medium consists of water alone or a mixture of water and at least one member selected from the group consisting of inorganic acids, organic acids, alcohols, halogenated ketones and halogenated hydrocarbons.

8. The process according to claim 7, wherein the aqueous medium is water.

9. The process according to claim 1, wherein the water in the aqueous medium is present from the beginning of the reaction.

10. The process according to claim 1, wherein the water in the aqueous medium is added during the course of the reaction.

11. The process according to claim 1, wherein the fluorine or fluorine fluorosulfonate is used for the reaction in a dilute form with an inert gas.

12. The process according to claim 11, wherein the inert gas is nitrogen.

13. The process according to claim 1, wherein the cytosine compound is used in the form of a salt.

14. The process according to claim 1, wherein the fluorine or fluorine fluorosulfonate is used in an amount of not less than 1 mol to 1 mol of the cytosine compound.

15. The process according to claim 1, wherein said cytosine compound is reacted with fluorine fluorosulfonate.

16. The process according to claim 1, wherein the reaction is followed by heating the reaction mixture at a temperature higher than that as adopted in the reaction with fluorine or fluorine fluorosulfonate.

17. The process according to claim 16, wherein the temperature of heating is from 60° to 100° C.

18. The process according to claim 17, wherein the heating is carried out for a period of 1 to 6 hours.

19. The process according to claim 16, wherein the heating is carried out at a pH of 1 to 9.

* * * * *